United States Patent
Fox et al.

(10) Patent No.: US 10,329,022 B2
(45) Date of Patent: Jun. 25, 2019

(54) ADJUSTABLE SENSOR OR SENSOR NETWORK TO SELECTIVELY ENHANCE IDENTIFICATION OF SELECT CHEMICAL SPECIES

(71) Applicant: HONEYWELL INTERNATIONAL INC., Morris Plains, NJ (US)

(72) Inventors: Richard Bryce Fox, San Tan Valley, AZ (US); Henry Au, West Covina, CA (US); Dacong Weng, Rancho Palos Verdes, CA (US); Mike Koerner, Rancho Palos Verdes, CA (US); Dennis Morita, Rancho Palos Verdes, CA (US)

(73) Assignee: HONEYWELL INTERNATIONAL INC., Morris Plains, NJ (US)

(*) Notice: Subject to any disclaimer, the term of this patent is extended or adjusted under 35 U.S.C. 154(b) by 218 days.

(21) Appl. No.: 15/339,405

(22) Filed: Oct. 31, 2016

(65) Prior Publication Data

US 2018/0118351 A1    May 3, 2018

(51) Int. Cl.
  *B64D 13/00*  (2006.01)
  *G01N 33/00*  (2006.01)
  (Continued)

(52) U.S. Cl.
  CPC .............. *B64D 13/00* (2013.01); *B64D 13/06* (2013.01); *G01N 27/12* (2013.01);
  (Continued)

(58) Field of Classification Search
  CPC ............ B64D 13/00; B64D 2013/0603; B64D 13/06; B64D 2013/0618;
  (Continued)

(56) References Cited

U.S. PATENT DOCUMENTS 5,497,651 A    3/1996  Matter et al.
5,571,401 A   11/1996  Lewis et al.
(Continued)

FOREIGN PATENT DOCUMENTS

EP    1923697 A1    5/2008
EP    3050801 A1    8/2016
(Continued)

OTHER PUBLICATIONS

Search Report from EP application No. 17198105.3 dated Mar. 2, 2018.

*Primary Examiner* — Shogo Sasaki
(74) *Attorney, Agent, or Firm* — Shimokaji IP

(57) ABSTRACT

An environmental control system (ECS) having contaminants in supply air that flows into an environment includes an outside air contaminant component that senses contaminants in outside air, wherein the outside air contaminant component is upstream of the environment, A recirculated air contaminant component is provided and that senses contaminants in recirculated air supplied by the environment, wherein the recirculated air contaminant component is downstream of the environment. A voltage supply provides a non-linear variable voltage to at least one of the components. A controller is in communication with the components and the voltage supply; wherein, upon a measured resistance, from at least one of the components, that exceeds a threshold, the controller varies at least one of an outside air flow and a recirculated air flow in the ECS.

3 Claims, 11 Drawing Sheets

(51) Int. Cl.
*B64D 13/06* (2006.01)
*G01N 27/12* (2006.01)

(52) U.S. Cl.
CPC ..... *G01N 33/0027* (2013.01); *G01N 33/0047* (2013.01); *B64D 2013/0603* (2013.01); *B64D 2013/0618* (2013.01); *B64D 2013/0688* (2013.01); *Y02T 50/56* (2013.01)

(58) Field of Classification Search
CPC ....... B64D 2013/0688; G01N 33/0027; G01N 27/12; G01N 33/0047
See application file for complete search history.

(56) References Cited

U.S. PATENT DOCUMENTS

| | | | |
|---|---|---|---|
| 5,627,305 | A | 5/1997 | Yun et al. |
| 6,493,638 | B1 | 12/2002 | McLean et al. |
| 7,597,788 | B2 | 10/2009 | Visel et al. |
| 7,950,271 | B2 | 5/2011 | Novak et al. |
| 2006/0054025 | A1 | 3/2006 | Kang et al. |
| 2007/0086921 | A1* | 4/2007 | Visel ................. B82Y 15/00 422/88 |
| 2011/0259080 | A1 | 10/2011 | Ratcliffe et al. |
| 2013/0211732 | A1 | 8/2013 | Chuang |
| 2015/0293057 | A1 | 10/2015 | Mohanty et al. |

FOREIGN PATENT DOCUMENTS

| | | | |
|---|---|---|---|
| WO | 0241095 | A1 | 5/2002 |
| WO | 2011095257 | A1 | 8/2011 |

\* cited by examiner

| COMPOUND | LOW Ug/M3 50th PERCENTILE | MEDIUM Ug/M3 75th PERCENTILE | HIGH Ug/M3 95th PERCENTILE | COMMERCIAL USES OR SOURCES ||| 
|---|---|---|---|---|---|---|
| | | | | CABIN | ENGINE GENERATED BLEED | ENGINE INGESTED BLEED |
| ACETALDEHYDE | 7.1 | 13.3 | 36.9 | SECONDARY REACTION PRODUCT FROM VOC+O3 | ENGINE OIL | ENGINE EXHAUST |
| ACETONE | 21.4 | 34.5 | 73.2 | HUMAN BIOEFFLUENT | ENGINE OIL | ENGINE EXHAUST |
| ACETONITRILE | 11.4 | 19.3 | 118 | | ENGINE OIL | ENGINE EXHAUST |
| BENZALDEHYDE | 0.5 | 1.3 | 4.2 | FOOD FLAVORING | ENGINE OIL | ENGINE EXHAUST |
| BENZENE | 0.5 | 1.8 | 4.4 | | | ENGINE EXHAUST |
| BUTANAL | 0.1 | 1.0 | 5.4 | | ENGINE OIL | ENGINE EXHAUST |
| 2-BUTANONE | 2.5 | 4.9 | 14.8 | | ENGINE OIL | ENGINE EXHAUST |
| CARBON DIOXIDE | 400 | 1000 | 5000 | HUMAN BIOEFFLUENT | | |
| CARBON MONOXIDE | 0.1 | 3 | 9 | | | ENGINE EXHAUST HYDRAULIC FLUID |
| n-DECANE | 0.1 | 0.5 | 1.3 | | | ENGINE EXHAUST |
| ETHANOL | 0.2 | 108 | 574 | BEVERAGE SERVICE | | |
| ETHYL ACETATE | 0.1 | 2.3 | 6.5 | | ENGINE OIL | |
| FORMALDEHYDE | 5.7 | 9.7 | 36.2 | | ENGINE OIL | ENGINE EXHAUST |
| n-HEXANE | 0.4 | 26.9 | 232 | | ENGINE OIL | ENGINE EXHAUST |
| METHYLENE CHLORIDE | 0.1 | 4.6 | 41 | | ENGINE OIL | |
| NAPHTHALENE | 0.1 | 0.3 | 0.6 | | | ENGINE EXHAUST |
| NONANE | 0.3 | 2.4 | 9.6 | | ENGINE OIL | |
| PROPANAL | 2.1 | 2.6 | 21.3 | | ENGINE OIL | |
| TOLUENE | 4.5 | 9.2 | 26.5 | | ENGINE OIL | ENGINE EXHAUST |
| ULTRA-FINE PARTICLES | 10,000 | 100,000 | 500,000 | | ENGINE OIL | ENGINE EXHAUST |
| VINYL ACETATE | 0.1 | 0.4 | 2.8 | CABIN CONTAMINANT | | |
| O, m- & p- XYLENE | 0.4 | 2.9 | 11.5 | | | ENGINE EXHAUST |

FIG. 3B

| SENSOR READING | RESPONSE |
| --- | --- |
| VOC SENSORS ON ALL MAIN ENGINES SUPPLYING BLEED AIR SIMULTANEOUSLY SHOW AN INCREASE IN RATE OF CHANGE OF $V_{OUT}$. | CLOSE BLEED AIR SUPPLY VALVES AND PLACE CABIN INTO 100% RECIRCULATION MODE. MODULATE SUPPLY VALVES EVERY TWO MINUTES UNTIL SENSOR RATE OF CHANGE INDICATES GROUND SOURCE OF CONTAMINATION IS GONE (EXAMPLE IS OF A TAXI LINE-UP). ONE COULD ALSO USE WEIGHT ON WHEELS SIGNAL AND IF SENSOR HAS NOT RETURNED TO BASELINE THEN OPEN BLEED VALVES ONCE WEIGHT ON WHEELS SENSORS INDICATED AIRCRAFT IS AIRBORNE. |
| VOC SENSORS ON ONE MAIN ENGINE SUPPLYING BLEED AIR SHOWS AN INCREASE IN RATE OF CHANGE OF $V_{OUT}$. | CLOSE BLEED AIR SUPPLY VALVE FOR THE ONE ENGINE SHOWING AN INCREASE RATE OF CHANGE. |
| VOC SENSORS ON APU SUPPLYING BLEED AIR SHOWS AN INCREASE IN RATE OF CHANGE OF $V_{OUT}$. | CLOSE APU BLEED AIR SUPPLY VALVE. IF ENGINES NOT OPERATIONAL, SEND WARNING TO COCKPIT OF FAULT IN BLEED AIR QUALITY. |
| HIGH RATE OF CHANGE FOR CABIN RETURN VOC SENSOR, BUT NOT RATE OF CHANGE INDICATED FOR BLEED SUPPLY VOC SENSORS. | INDICATION IS OF A CABIN SOURCE OF CONTAMINATION.<br>    A. INCREASE BLEED SUPPLY AND DECREASE RECIRCULATION RATE UNTIL $V_{OUT}$ RETURNS TO CLOSE BASELINE VALUES.<br><br>    B. IN THE EVENT AN ELECTRONIC AIR CLEANER IS WAITING ON A SIGNAL TO TURN ON, SUPPLY SIGNAL TO TURN ON ELECTRONIC AIR CLEANER (OR OPEN VALVE TO A FILTER THAT IS ONLY USED TO REMOVE CONTAMINATION DURING HIGH LEVELS OF CONTAMINATION). |
| HIGH RATE OF CHANGE OF VOC BELOW RECIRCULATION AIR PURIFIER (MAY BE A FILTER OR A PHOTOCATALYTIC OXIDATION UNIT, OR A COMBINATION OF THESE OR OTHER AIR PURIFICATION DEVICE). | SEND A NOTIFICATION TO THE COCKPIT THAT MAINTENANCE SHOULD CHECK AIR PURIFICATION UNIT FOR PROPER OPERATION AND PREFORM MAINTENANCE AS REQUIRED TO RESTORE NORMAL OPERATION. |
| VOC SENSORS ON CABIN RECIRCULATION ARE STABLE AT BASELINE VALUES. | ADAPTIVE OR MODIFIED ENVIRONMENTAL CONTROL SYSTEM SHOULD BE SENT SIGNAL TO REDUCE BLEED AIR SUPPLY VALUE UNTIL A CHANGE IN SENSOR OUTPUT IS DETECTED. THE VOC SENSOR $V_{OUT}$ READING MAY BE SET TO CONTROL CONTAMINANT LEVELS TO NOT EXCEED A PRESELECTED LEVEL TO CONSERVE ENERGY AND FUEL, BUT OPTIMIZING THE AMOUNT OF OUTSIDE DILUTION AIR TO PROVIDE ADEQUATE, BUT NOT A WASTEFUL AMOUNT OF OUTSIDE AIR TO MAINTAIN VOC AT A PROGRAMMED MAXIMUM VALUE REPRESENTATIVE OF LIMITS DEFINED BY ASHRAE STANDARD 62.1-2016. |

FIG. 9

ADJUSTABLE SENSOR OR SENSOR NETWORK TO SELECTIVELY ENHANCE IDENTIFICATION OF SELECT CHEMICAL SPECIES

BACKGROUND OF THE INVENTION

The present invention generally relates to apparatus and methods for treatment of airstreams in an Environmental Control System (ECS) to remove contaminants.

ECSs of various types and complexity are used in military and civil airplanes, helicopter, Mass Transit, Low Speed and High Speed Rail, and spacecraft applications. If fact, environmental control systems in buildings that manage energy consumption operate their systems by controlling contaminant levels or bringing in outside air to dilute contaminants, and require sensors for this process. In aircraft for example, airflow may be circulated to occupied compartments, cargo compartments, and electronic equipment bays. Air containing many pollutants such as particulate matter, aerosols, and hydrocarbons may range in humidity from dry (<2%) to very humid and may be delivered in a heated condition to the cabin from the ECS.

Occupants are not exposed to a single chemical in isolation, and the effects of co-exposures to multiple chemicals are poorly understood. Exposure duration for occupants can be 14+ hours. Air Crews can routinely be assigned to work up to a 16 hour duty day. The duty day can be extended up to the 16 hour limit if there is a maintenance delay or weather. Some international crews are assigned to work a longer duty day. Pilots are limited to flying no more than 100 hours per month, while cabin crew may work up to around 120 hours per month. There are flight safety and security implications for not adequately protecting pilots (who must perform cognitively-demanding safety-sensitive flight duties) and cabin crew (who must maintain cabin safety and security). Specifically, manufacturers are currently required to ensure that aircraft systems are designed to provide—in operation, under normal conditions and during any probable failure—"a sufficient amount of uncontaminated air to enable the crewmembers to perform their duties without undue discomfort or fatigue, and to provide reasonable passenger comfort." It has been widely recognized by air accident investigators, regulators, and pilot groups that flight safety can be compromised when pilots are exposed to oil-based contaminants in the ventilation air entering from outside the aircraft through the main engine bleeds or APU bleed or other air sources including ground supplies and electric compressors. Requiring pilots to rely on their noses to identify the presence and location of bleed air contaminants prolongs the exposure for the pilots and/or cabin occupants, depending on the location of the contaminant source.

Buildings and high density ground transit have similar concerns and constraints as aircraft.

Metal oxide and other kinds of sensors are generic in response when operated with a constant supply voltage and current at a constant environmental response. It is not possible to determine in a steady state operation mode what VOC contaminant might be present. At times it would be useful in a controlled environment when there are only a few major sources of VOC to be able to identify which VOC is being detected.

It is known that increasing or decreasing metal oxide sensor voltage may change the sensor response to a specific chemical. There may be many compounds present in a more closed environment such as an aircraft cabin or an office, or home. However, only a limited number of volatile organic compounds present are of concern. Ethanol may be present in higher concentrations in closed environments, but is not a significant concern from a control perspective, because it is present in significant quantities in alcoholic beverages. Formaldehyde, acetaldehyde, acrolein, and other aldehydes, on the other hand, are very irritating in low concentrations.

During a flight cycle, the air may have more organic contaminants at ground level through top of climb. It is more likely during these flight stages to sense aldehydes than during cruise phase. During meal service, on the other hand, there may be little to no formaldehyde, but large quantities of alcohol.

As can be seen, there may be an ongoing need to identify the presence of certain VOC's and then enable corrective action to an ECS.

SUMMARY OF THE INVENTION

In one aspect of the present invention, an environmental control system (ECS) having contaminants in supply air that flows into an environment comprises an outside air contaminant component that senses contaminants in outside air, wherein the outside air contaminant component is upstream of the environment; a recirculated air contaminant component that senses contaminants in recirculated air supplied by the environment, wherein the recirculated air contaminant component is downstream of the environment; a voltage supply that provides a non-linear variable voltage to at least one of the components; and a controller in communication with the components and the voltage supply; wherein, upon a measured resistance, from at least one of the components, that exceeds a threshold, the controller varies at least one of an outside air flow and a recirculated air flow in the ECS.

In another aspect of the present invention, a contaminant detection system comprises a component configured to respond at a plurality of voltages including a first voltage and a second voltage; wherein the plurality of voltages are provided to the component in a continuous, multiple sweeping fashion over a range of voltages that includes the first and second voltages; wherein, at the first voltage, the component can provide a first resistance response; wherein, at the second voltage, the component can provide a second resistance response; wherein the first and second voltages are different; wherein the first and second resistance responses are different; wherein, when the first resistance response meets or exceeds a first threshold, a presence of a first contaminant is indicated; and wherein, when the second resistance response meets or exceeds a second threshold response, a presence of a second contaminant is indicated.

In yet another aspect of the present invention, a method of controlling contaminants in an environment comprises placing one of a sensor and a sensor array at a location that is at least one of upstream of the environment and downstream of the environment; wherein one of the sensor and sensor array receives a supply air that is one of outside air that comes from a source other than the environment and recirculated air that comes from the environment; supplying a varying voltage to one of the sensor and sensor array; measuring resistance of one of the sensor and sensor array; using the voltage and respective measured resistance to identify at least one contaminant; using the identified contaminant to identify a source of the identified contaminant; and adjusting an amount of at least one of the outside air and the recirculated air into the environment to at least reduce a concentration of the identified contaminant.

These and other features, aspects and advantages of the present invention will become better understood with reference to the following drawings, description and claims.

BRIEF DESCRIPTION OF THE DRAWINGS

FIG. 3B is a table depicting concentrations of contaminants in air samples from various air sources according to an exemplary embodiment of the present invention;

FIG. 9 is an exemplary algorithm that describes potential corrective action that can be taken by a controller according to an embodiment of the present invention.

DETAILED DESCRIPTION OF THE INVENTION

Figure 1A:
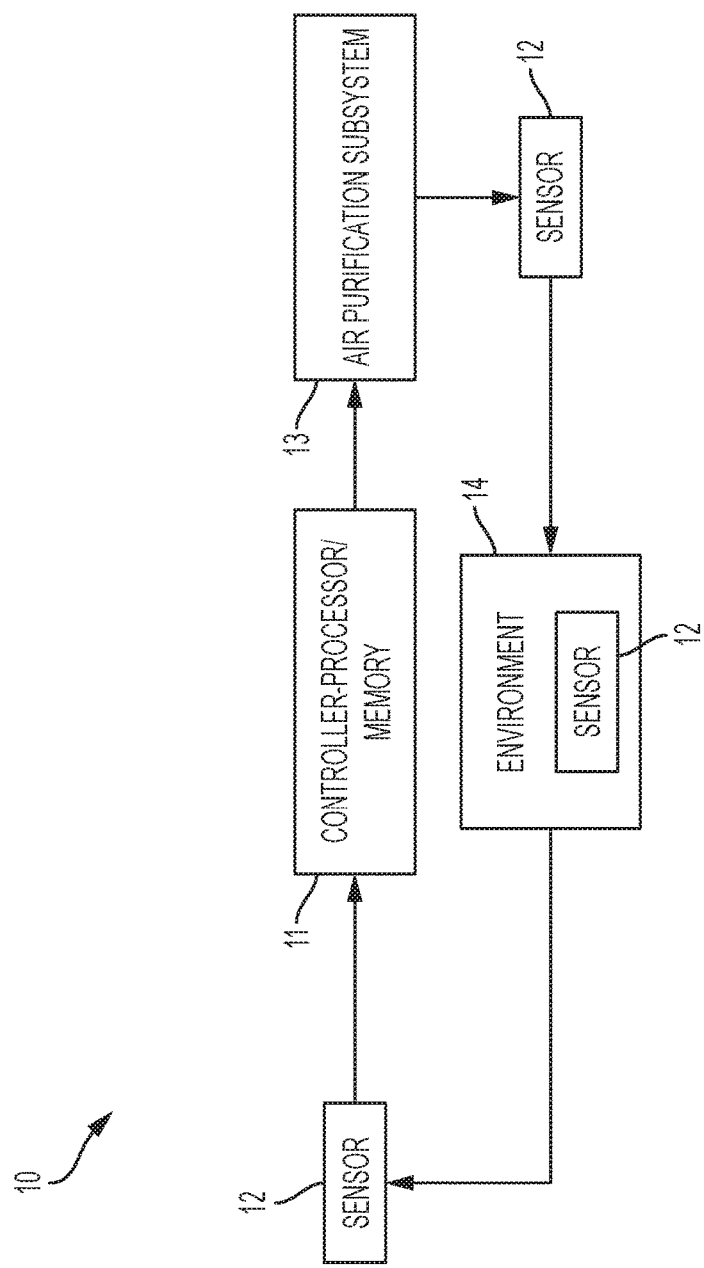
FIG. 1A is a block diagram of an environmental control system according to an exemplary embodiment of the present invention.

The following detailed description is of the best currently contemplated modes of carrying out the invention. The description is not to be taken in a limiting sense, but is made merely for the purpose of illustrating the general principles of the invention, since the scope of the invention is best defined by the appended claims.

Various inventive features are described below that can each be used independently of one another or in combination with other features. However, any single inventive feature may not address any of the problems discussed above or may address only one of the problems discussed above. Further, one or more of the problems discussed above may not be fully addressed by any of the features described below.

As will be appreciated by one skilled in the art, aspects of the present invention may be embodied as a system, method, or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable media having computer readable program code embodied thereon.

Any combination of one or more computer readable storage media may be utilized. A computer readable storage medium is an electronic, magnetic, optical, or semiconductor system, apparatus, or device, or any suitable combination of the foregoing. More specific examples (a non-exhaustive list) of the computer readable storage medium would include the following: a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium is any tangible medium that can store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable storage medium that can direct a computer, other programmable data processing apparatus, or other devices to function in a particular manner, such that the instructions stored in the computer readable storage medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Broadly, the present invention provides an environmental control system (ECS) that can continuously detect changing contaminants—both in kind and degree—in contaminated air in the ECS. The contaminated air may include outside air entering the ECS through engines or APU, or other air sources including ground supplies and electric compressors, as well as recirculating air in the ECS. A controller of the ECS may receive contamination signals from one or more sensors that sense one or more contaminants in the contaminated air.

Information on contaminants being sensed by a sensor may be gained by sweeping a voltage to the sensor, and monitoring the sensor output resistance or voltage. Different classes of contaminants will respond in different manners to the change in sensor voltage, termed here as Temperature Programmed Oxidation (TPO) and can be characterized by the range of voltage or voltages that may elicit a response for that class of compound/contaminant during the sweeping of the voltage.

The sweeping of voltage could be in any number of forms. The current could rise and fall in a sinusoidal pattern. Alternatively, it could rise and fall in a saw tooth pattern.

With a single sensor, a controlled change to an input voltage to the sensor can be provided while continuously monitoring sensor response. Continuously ramping the voltage up or down at a fixed rate, while monitoring changes in sensor resistance output, can indicate the type of contaminant present—whether there is only a single contaminant or multiple contaminants. The sensor signals can be supplied to a processor that evaluates the signals against a sensor signal baseline. The processor, knowing the phase of environment operation from an input, such as a pressure transducer, can determine whether corrective action to a signal should or should not be implemented.

With an array of sensors, each sensor can be tuned with a sensor input voltage that is specific to a contaminant class. The array of sensors may simultaneously return signals to a processor more rapidly than a single sensor. A sensor array may enable an ECS to identify and respond to a VOC contaminant in a more rapid fashion. One of the sensors in the array could be tuned to monitor ozone. A benefit of a sensor array is that it provides an element of sensor redundancy in the event of a failure of one of the sensors.

FIG. 1 is a block diagram of an ECS 10 according to an exemplary embodiment of the present invention. The ECS 10 may include a controller 11, such as a computer having a processor and a memory, in continuous or intermittent communication with an air purification subsystem 13 and one or more sensors 12. The sensors 12 may be positioned in various points throughout the ECS to sense contaminants in, and/or air characteristics of, the outside air supplied through engine or APU bleeds or other air sources including ground supplies and electric compressors, and/or recirculating air in the ECS and/or, in particular, an environment 14, such an aircraft cabin. The contaminants in the ECS may include, for example, VOCs, SVOCs, formaldehyde, acetaldehyde, acrolein and other aldehydes, ultrafine particles (UFPs), carbon monoxide, carbon dioxide, and ozone.

One or more of the sensors 12 can be any sensor capable of sensing the anticipated contaminants in the contaminated air. One or more of the sensors can sense the identity and amount of the individual contaminants in the contaminant air. For example, at least three classes of solid state gas sensors could be employed, individually or in combination, by this invention.

One class of solid state gas sensors is cyclic voltammetry (CV) which is an electrochemical technique that measures the current that develops in an electrochemical cell under conditions where voltage is in excess of that predicted by the Nernst equation. CV measurement may cycle the potential of a working electrode and measure the resulting current.

A second class of sensors is catalytic combustion sensors (CCS).

CCS could use temperature programmable oxidation in hot wire sensors, sometimes known as "pellistor" or catalytic bead sensors, platinum wire sensors, or other metal or doped polymer membrane sensors.

A third class of sensors include conductometric or chemiresistance based gas sensors. Conductometric sensors includes the range of formulations of metal oxides synthesized in the form of porous ceramics that may be used to create metal oxide sensors.

One or more of the sensors 12 can be any sensor capable of sensing anticipated air characteristics, such as temperature and pressure or gas composition, of the contaminated air. For example, to sense temperature and pressure, part numbers 51090026-51 and 1090030-51 by Honeywell for temperature and pressure sensors could be used.

The controller 11 can include a processor and a memory that can store instructions to be executed by the processor to implement a method of removing contaminants from, and/or change air characteristics in, a space to be occupied by humans, such as the cabin of an aircraft, according to the present invention. The controller 11 may receive contamination signals from sensor(s) 12 which may sense contaminants from, for example, a cabin filter, a filter to a mix manifold, an ECS pack to the mix manifold, and/or the mix manifold to the cabin. The controller 11 may also receive contamination signals from sensor(s) 12 which may sense contaminants in bleed air coming from, for example, one or more engines and/or an auxiliary power unit (APU). Likewise, the controller 11 may receive characteristic signals from sensor(s) 12 which may sense air characteristics from, for example, the cabin. The characteristics may include temperature and pressure.

The controller 11 may then compare the contamination signals and/or characteristic signals to one or more thresholds that may relate to, for example, cabin pressure, cabin temperature, particulate mass and VOC concentrations. In the example of VOC concentrations, the controller 11 may compare contamination signals to a contaminant concentration look up table that may have information/data of contaminant class and/or contaminant concentration versus sensor response (e.g., resistance/current) and applied voltage.

In the example of air characteristics, the controller may compare air characteristic signals to a look up table that may have information/data of temperature requirements in a cabin as promulgated by a government agency. A similar comparison may occur for the air characteristic of pressure in a cabin.

Based on the foregoing comparison(s), the controller 11 may then command a valve to alter valve opening/closing and thereby alter a flow of outside air. Also, in addition to or in lieu of the foregoing command, the controller may command a fan to alter a fan speed of recirculated air. Alternatively, the response of the controller may be to modulate an air purification device, increasing or decreasing its power to effect the desired change in air contaminant concentrations.

Either alone or in combination with commanding the valve and the fan, the controller may command an outflow valve to open or close. The valve may enable combined outside and recirculated air to enter the cabin as cabin air.

Figure 1B:
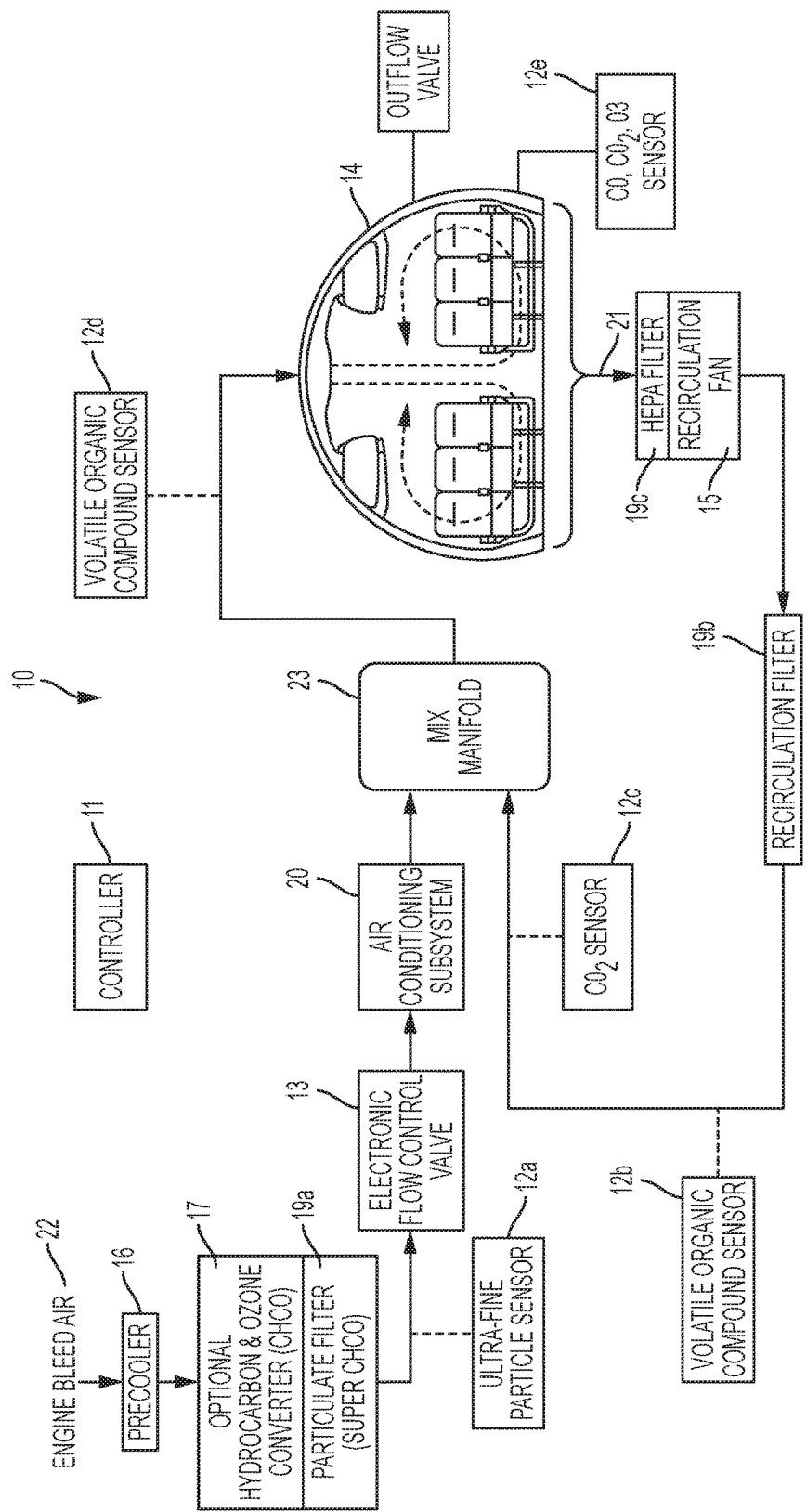
FIG. 1B is a block diagram of an environmental control system that can be implemented in the system of FIG. 1A according to an exemplary embodiment of the present invention.

FIG. 1B is an exemplary embodiment of the ECS 10 depicted in FIG. 1A. The controller 11 may control one or more of the components and/or subsystems of the ECS 10. The ECS 10 may include a pneumatic bleed air precooler 16 that cools outside or bleed air 22 supplied through engine or APU bleeds and/or other air sources including ground supplies and electric compressors, entering the ECS 10. The outside air 22 supplied through engine or APU bleeds or other air sources including ground supplies and electric compressors, may have contaminants that, at certain levels, may be undesirable for occupants in the environment 14. The pneumatic bleed air precooler 17 may be of any design well known in the art, such as a pneumatic bleed air precooler made by Honeywell International Inc. ("Honeywell"), part number 2341788-1. The pneumatic bleed air precooler 16 may cause a cooling in air temperature whereby, upon cooling, the temperature of the air exiting the pneumatic bleed air precooler 16 can be, in embodiments, in a range of from about 135° C. to about 260° C., or from about 135° C. to about 200° C., or from about 135° C. to about 150° C.

A hydrocarbon and ozone converter 17 may receive air from the precooler 16 and convert hydrocarbons and ozone in the air to compounds that are believed to be non-harmful to humans. The converter 17 may be of any design well known in the art, such as an ozone converter made by Honeywell, part number 2341590-1, or a volatile organic compound and ozone converter made by Honeywell, part number 67200008-00. The converter 17 may convert a percentage of the total hydrocarbons wherein, in embodiments, the amount of hydrocarbons in the air exiting the converter 17 may be in a range of from about 0 ug/M3 to about 4000 ug/M3, or from about 0 ppmV to about 0.5 ppmV isobutylene equivalents, or from about 0 ug/M3 to about 500 ug/M3 isobutylene equivalents, or from about 0 ppmV isobutylene equivalents to about 0.1 ppmV isobutylene equivalents. The converter 17 may convert a percentage of the total ozone wherein the amount of ozone in the air existing the converter 17 may be, in embodiments, in a range of from about 0 ppmV to about 0.1 ppmV, or from about 0 ppmV to about 0.25 ppmV.

A particulate filter 19a may receive air from the converter 17 to filter out particulates of a desired size. In embodiments, the particulates exiting the filter 19a can be, in embodiments, of a size of from about 0 um to about 0.3 um for 99% HEPA filtration at 0.3 um. The filter 19a may be of any design well known in the art, such as a filter made by Honeywell SP Defense under the trade name FMM7™. In addition, the filter may contain additional beds of adsorbent to remove aldehydes and ultrafine particles with a size range of 10 to 200 nm that are products of synthetic oil decomposition.

A particle sensor 12a may be downstream of the filter 19a to sense a particle count per cubic centimeter or contaminant mass concentration. The particle count concentration or mass contaminant concentration may be for one or more contaminants—for example, contaminants including but not limited to VOCs adhered to carbon and SVOC aerosol. For example, the sensor 12a may sense particle count or concentrations, in embodiments, of from about 0 particles/cm$^3$ to about 1,000,000 particles/cm$^3$ (for aircraft takeoff), or from about 0 particles/cm$^3$ to about 400,000 particles/cm$^3$ (for aircraft landing), or from about 0 particles/cm$^3$ to about 800,000 particles/cm$^3$ (for aircraft descent), or from about 0 particles/cm$^3$ to about 100,000 particles/cm$^3$ (for aircraft cruise) or a mass concentration of from about 0 ug/M3 to about 100,000 ug/M3, or from about 0 ug/M3 to about 4000 ug/M3, or from about 0 ug/M3 to about 500 ug/M3, or from about 250 ug/M3 to about 400 ug/M3. The sensor 12a may then send intermittent or continuous particle count or mass contaminant concentration signals to the controller 11, such as when the mass contaminant concentration exceeds/equals a threshold and/or falls below a threshold.

A flow control valve 13 may be downstream of the sensor 12a to control the amount and/or rate of air from the filter 19a, to an air conditioning subsystem 20, and eventually to an environment 14. The valve 13 may receive command signals from the controller 11 to alter the air flow amount or rate entering the air conditioning subsystem 20. The valve 13 may change or meter a rate of air flow wherein, in embodiments, a flow rate is of from about 0 to about 5000 cubic feet per minute recirculation flow (for a large wide body aircraft), or from about 0 to about 2500 cubic feet per minute recirculation flow (for a narrow body aircraft), or from about 0 to about 300 M3 per hour for a single filter. The size and number of filters can be changed to maintain filter face velocity within allowable filter performance requirements. The valve 13 may be of any design well known in the art, such as a 3.0 inch diameter electric motor modulating valve, part number 3205034-4, made by Honeywell.

An air conditioning subsystem 20 may be downstream of the valve 13. The subsystem 20 may alter the temperature and/or pressure of the air from the valve 13, and may be, for example, Engine Bleed Air System, Pneumatic Air Distribution System, Honeywell PN 6217C000-016. In embodiments, the air exiting the subsystem 20 may have a temperature of from about −10° C. to about 0° C., or from about 5° C. to about 27° C., or from about 15° C. to about 25° C. and mixed with hot bleed air 22 to obtain supply temperatures within about 18° C. to about 29° C. In embodiments, the air exiting the subsystem 20 may have a pressure of from about 11 psia to about 15 psia, or from about 12 psia to about 15 psia, or from about 13 psia to about 15 psia.

A mix manifold 23 may be downstream of the air conditioning subsystem 20. The manifold 23 can mix air from the air conditioning subsystem 20 and the cabin recirculation fan (such as a fan by Honeywell, part number 606772-1) and distribute it to the cabin 14. The hot trim air (bleed air) 22, controlled by a valve (such as a 2 inch diameter trim air valve by Honeywell, part number 3291978-00), can be inserted into the cool air from the mix manifold 23 prior to entering the cabin to control air temperature within a range of from about 18° C. to about 29° C. (for normal aircraft operating conditions), or from about 15° C. to about 20° C. (to precool the cabin), or from about 30° C. to about 40° C. (to pre-heat the cabin). For example, the ratio of volume of outside air 22 supplied through engine or APU bleeds or other air sources including ground supplies and electric compressors, to volume of recirculated air 21 may be, in embodiments, of from about 60 to about 100% (in normal aircraft operation), or from about 0% (if there was an adverse contamination event outside the aircraft, such as aircraft de-icing) to about 100%. The manifold 23 may be of any design well known in the art, such as a manifold made by Triumph Group.

A sensor 12*d*, such as a VOC sensor, may be downstream of the mix manifold 23. Although referred to as a VOC sensor, the sensor 12*d* is not intended to be limited to VOCs, but may also sense a combination of VOCs and SVOCs as an example. The sensor 12*d* may sense concentrations of one or more contaminants to verify that the mixed air exiting the manifold 23 meets certain requirements for occupant comfort in the environment 14. The requirements may be government regulatory requirements that address maximum limits for, example, CO, CO2, formaldehyde, acetaldehyde, acrolein, other aldehydes, ozone, VOC, SVOC, UFP between 10 nm and 200 nm diameter, and regulated particulates (PM2.5 and PM10). In other words, the maximum limits can be thresholds that should not be exceeded. Accordingly, for example, the sensor 12*d* may sense contaminant concentrations, in embodiments, of from about 0 ppmV to about 1 ppmV, or from about 0 ug/M3 to about 4000 ug/M3, or from about 0 UFP/cm3 to 1,000,000 UFP/cm3 with a center point of about 500,000 UFP/cm3, recognized in recent research as being associated with odors. The sensor 12*d* may then send intermittent and/or continuous concentration contamination signals to the controller 11, particularly when the contaminant concentration exceeds/equals a threshold and/or falls below a threshold.

From the sensor 12*d*, the mixed air (i.e., supply air) from the manifold 23 may enter the environment 14 where additional contaminants may be added to the supply air. As an example, the additional contaminants may come from occupants and/or food in the environment 14.

One or more sensors 12*e* may be within the environment 14 to sense air characteristics, such as temperature and/or pressure, of the supply air in the environment 14. Thus, the sensor(s) 12*e* may verify that the supply air meets certain requirements, such as government regulatory requirements, or does not exceed maximum limits, for occupant comfort in the environment 14. In other words, the maximum limits can be thresholds that should not be exceeded. Accordingly, for example, a sensor 12*e* may sense temperature, in embodiments, of from about 18° C. to about 29° C. As another example, a sensor 12*e* may sense pressure, in embodiments, of from about 11 psia to about 15 psia, or from about 12 psia to about 15 psia, or from about 13 psia to about 15 psia. The sensor(s) 12*e* may then send intermittent and/or continuous air characteristic signals to the controller 11, particularly when one or more characteristics exceed/equal one or more thresholds and/or fall below one or more thresholds.

Recirculated air 21 from the environment 14 may then exit to a filter 19*c*, which may be a high efficiency particulate absorption (HEPA) filter of any design well known in the art, such as a filter made by Honeywell under the trade name FMM7. The filter 19*a* may remove particulates from the recirculated air 21 of a desired size, such as, in embodiments, particulates of a size of from about 0 um to about 0.3 um at 99% removal efficiency.

A recirculation fan 15 may be downstream of the filter 19*c* to modulate the flow of recirculation air 21 inversely with outside air 22 supplied through engine or APU bleeds or other air sources including ground supplies and electric compressors, and thereby maintain a ventilation rate of the recirculation air 21 exiting the environment 14. As an example, a ventilation rate may be in embodiments of from about 0 to about 5000 CFM for total recirculation flow (for a large wide body aircraft), or from about 0 to about 2500 CFM (for a narrow body aircraft), or sufficient filter area to maintain about 400 feet per minute filter face velocity. The fan 15 may be of any design well known in the art, such as a fan made by Honeywell, part number 606772-1.

A recirculation filter 19*b* may be downstream of the fan 15. The filter 19*b* may remove particulates from the recirculated air 21 of a desired size, such as, in embodiments, particulates of a size of from about 0 to about 0.3 um at 99% removal efficiency, or from about 0 to about 1 um at 97% efficiency, or from about 0 to about 2.5 um for non-HEPA filtration. The filter 19*b* may be of any design well known in the art, such as a filter made by Honeywell under the trade name FMM7.

A sensor 12*b*, such as a VOC sensor, may be downstream of the filter 19*b*. The sensor 12*b* may sense concentrations of one or more VOCs in the recirculated air 21. Although referred to as a VOC sensor, the sensor 12*b* is not intended to be limited to VOCs, but may also sense SVOCs. For example, the sensor 12*b* may sense VOC contaminant concentrations from about 0 ppmV to about 1 ppmV, or from about 0 ug/M3 to about 4 ug/M3, or from about 0 UFP/CM3 to about 500,000 UFP/CM3. The sensor 12*b* may then send a VOC concentration contamination signal to the controller 11.

A sensor 12*c*, such as a carbon dioxide sensor, may be downstream of the sensor 12*b*. The sensor 12*c* may sense concentration of carbon dioxide in the recirculated air 21. For example, the sensor 12*c* may sense carbon dioxide contaminant concentrations, in embodiments, of from about background (about 400 ppmV) to about 5000 ppmV, or from about 800 ppmV to about 2000 ppmV, or from about 800 ppmV to about 1500 ppmV. The sensor 12*c* may then send intermittent and/or continuous carbon dioxide concentration contamination signals to the controller 11, particularly when a carbon dioxide concentration exceeds/equals a threshold and/or falls below a threshold. Downstream of the sensor 12*c* is the mix manifold 23.

As can be seen in FIG. 1B, during operation, the ECS 10 can adapt to changing contaminants and/or particulates and/or air characteristics in both the outside air 22 supplied through engine or APU bleeds or other air sources including ground supplies and electric compressors, and recirculated air 21. For example, the changes can occur as an aircraft moves from one operating mode to another, such as from taxing, to takeoff, to cruise at, for example, about 35,000 feet. The ECS 10 can adapt to the change by receiving intermittent and/or continuous signals from sensors, such as sensors 12*a*, 12*b*, 12*c*, 12*d*, and 12*e*. These signals can be generated when a parameter exceeds/equals a threshold and/or falls below a threshold. In response to a signal, the controller 11 may command a change to the operation of the flow control valve 13, the air conditioning subsystem 20, the mix manifold 23, and/or recirculation fan 15.

Figure 2:
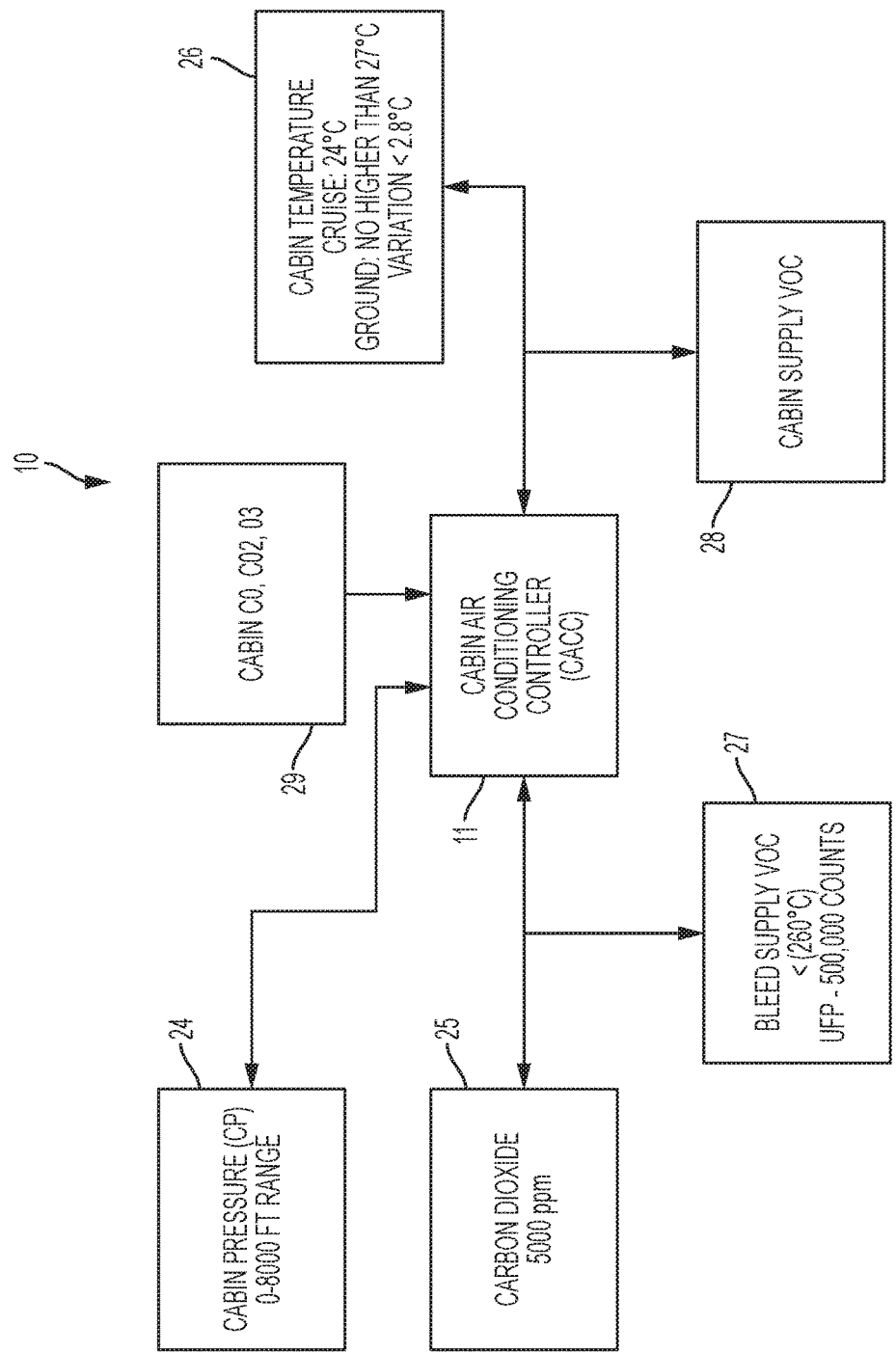
FIG. 2 is a flow chart of an operation of a controller in an environmental control system according to an exemplary embodiment of the present invention.

In FIG. 2, a flow chart depicts an exemplary operation of the controller 11. For example, the controller 11 may control pressure 24 in the cabin 14 as the cabin 14 (i.e., aircraft) moves between, for example, 0 to 35,000 feet in altitude—going from taxi to cruise and then to landing. Thus, the controller 11 may increase and decrease pressure 24 as the cabin changes altitude. For example, the controller 11 may maintain the cabin pressure 24, in embodiments, of from about 11 psia to about 15 psia, which may be equivalent to what an occupant might experience outside of the cabin between 0 to 8000 feet.

The controller 11 may, in embodiments, control carbon dioxide concentration 25 outside of the cabin 14 such that the concentration does not exceed about 5000 ppm. Accordingly, in an exemplary embodiment, if the carbon dioxide concentration in the recirculated air reaches about 2000 ppm, the controller 11 may command that an outside air 22 inflow rate be increased. In another exemplary embodiment, if the carbon dioxide concentration in the recirculated air falls below about 800 ppm, the controller 11 may command that an outside air 22 flow inflow be decreased.

The controller 11 may control cabin temperature 26 in the cabin 14. For example, during cruise of the aircraft, the cabin temperature 26 may have a threshold at about 24° C.; while on the ground, the cabin temperature may have a threshold of no more than about 27° C.; with a temperature variation at all times being less than about 5° C. These temperatures may be maintained by the controller 11 commanding a change in the air conditioning subsystem 20, for example, by decreasing trim air 16 from the hot system, or increasing the cold air from the air cycle machine 20 to maintain the temperature set-point.

The controller 11 may control bleed air VOCs 27 into the cabin 14. In embodiments, the bleed air 22 may be from one or more aircraft engines and/or an APU. In embodiments, when the bleed air 22 is maintained at no more than about 260° C. after exiting the precooler, a particle sensor, such as sensor 12a, may have an ultra-fine particle count threshold of about 200,000 to 250,000 UFP/cm3. In other embodiments, if the particle count for one bleed air source exceeds the particle count of the other bleed air sources—over two flight cycles of take-off and landing—the controller 11 may command the manifold 23 to reduce the bleed air 22, increase the recirculation air 21, and send a note to the flight maintenance system (not shown) to recommend further evaluation.

The controller 11 may control cabin supply air VOCs 28 coming from the mix manifold 23 and into the cabin 14. VOC sensors (i.e., contaminant sensors for VOCs and other contaminants) may have, in some embodiments, a contaminant threshold.

In embodiments, VOC sensors may monitor VOCs and other compounds upstream and downstream of air purification filters, such as filters 19b and 19c. In other embodiments, VOC sensors may monitor VOCs and other compounds downstream of an air cycle machine, such as one in the air conditioning subsystem 20. In further embodiments, VOC sensors may monitor VOCs and other compounds at the exit of a mix manifold, such as manifold 23.

The controller 11 may control carbon monoxide, carbon dioxide, VOC, aldehydes, UFP, and/or ozone 29 in the cabin 14 through the use of one or more sensors. In embodiments, a carbon monoxide threshold may be from about or 9 ppmV (the US EPA recommended limit) to about 50 ppmV (the FAA maximum allowed), a carbon dioxide threshold may be from about 800 ppmV to 2000 ppmV (but not to exceed 5000 ppmV, the FAA limit), and an ozone threshold may be from about 0.1 ppmV to about 0.25 ppmV (for short durations). When one or more of these thresholds is exceeded, the controller 11 may command the manifold to increase bleed air 22, according to various embodiments.

Figure 3A:
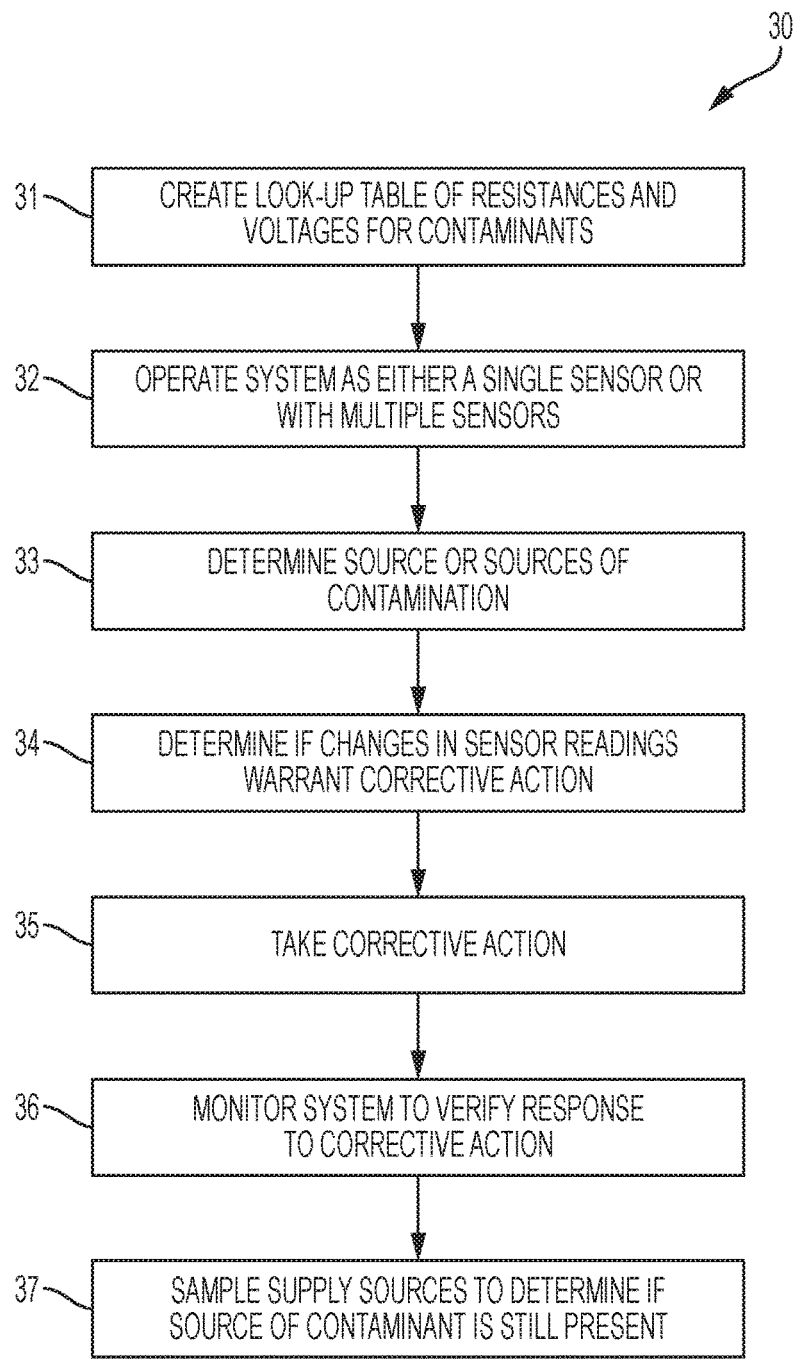
FIG. 3A is a flow chart of a method of sensing contaminants and taking corrective action according to an exemplary embodiment of the present invention.

FIG. 3A is a flow chart of an exemplary method 30 of identifying contaminants and taking corrective action to reduce or eliminate the contaminants at their source according to the present invention. In a step 31 a look up table may be created of contaminants, contaminant concentrations, contaminant sources, sensor response, and/or applied voltage.

In a step 32, a controller may receive sensor response or contaminant signal(s) from one or more individual sensors (or sensor arrays) in the ECS.

In a step 33, the controller may compare the received contaminant signal(s) to the information/data in the look up table, such as sensor response(s). The sensor response(s) may relate to resistance response of the respective sensor (or sensor array). Based on the sensor response(s), a contaminant(s) may be determined/identified and, in turn, a contaminant source(s) may be determined/identified.

In a step 34, the foregoing sensor response(s) may also be compared to a sensor or contaminant threshold. The threshold may relate to a minimum sensor response and/or minimum contaminant response below which the controller will not initiate corrective action. At or above the threshold, the controller may initiate corrective action.

In a step 35, when the sensor response is at or above the threshold, the controller may initiate corrective action. The corrective action can be based on the above identified contaminant source(s). Accordingly, the corrective action may be, for example, the operation of valves and/or filters and/or fans in the ECS as described above.

In a step 36, after corrective action has been initiated, the controller may continue to receive sensor/contaminant signal(s), continue to compare the sensor response(s) to the threshold, and continue to take corrective action if the sensor response(s) is at or above the threshold. Once the sensor response(s) falls below the threshold, the controller may stop the corrective action.

In a step 37, in a continuous or intermittent fashion as the above steps are carried out, the contamination source(s) in the look up table can be sampled to determine if the contaminant is present.

FIG. 3B is an exemplary look up table for use in step 31 of FIG. 3A. The look up table can list frequently occurring contaminants in bleed air and/or cabin air and/or recirculating air in an ECS of an aircraft, according to an embodiment. Also shown for each contaminant is concentration at a plurality (e.g., three) different levels and a potential source(s) of each contaminant. Sensor response information/data (e.g., resistance and/or voltage) can be added to the table. The sensor response data for one or more of the contaminants listed in FIG. 3B may be developed in the following fashion.

Single Sensor Embodiment

In an exemplary embodiment employing a "single sensor", one sensor can be used to identify multiple contaminants. The "single sensor" may be located in one or more of the positions occupied by the sensors 12 shown in FIGS. 1A-1B.

Figure 4A:
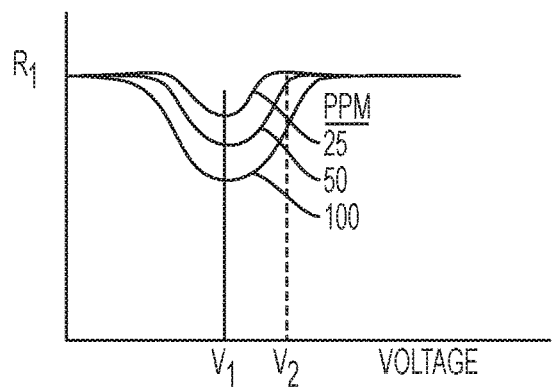
FIG. 4A is a graph of resistance versus voltage of a first contaminant at three different concentrations according to an exemplary embodiment of the present invention.

In FIG. 4A, a varying voltage may be applied to a sensor that is sensing a single contaminant identified in FIG. 3B. Sensing can occur at different contaminant concentrations and over an increasing voltage applied to the sensor. Resistance can be measured as the voltage increases. It can be seen from FIG. 4A that, for the particular contaminant in question, resistance $R_1$ drops from a baseline to a low or minimum (i.e., maximum resistance change) $R_{1MIN}$ at a voltage $V_1$. $R_{1MIN}$ may then be designated as a contaminant or sensor threshold 1. In embodiments, the threshold 1 can be a range. The threshold 1 can be determined at a plurality of contaminant concentrations to provide a different threshold for a respective different concentration of a single contaminant. For example, with three concentrations of contaminant 1, there may be thresholds 1A, 1B, 1C which do not overlap one another.

Accordingly, if a sensor is sensing an air flow, a varying voltage is being applied to the sensor, and sensor resistance drops to at least one of thresholds 1A-1C, at voltage $V_1$, one can conclude that contaminant 1 is present in the air flow. Knowing that contaminant 1 is present, one can then determine the source(s) of the contaminant from FIG. 3B. And, knowing which threshold 1A-1C was met or exceeded by the measured resistance, one can also determine the approximate concentration of contaminant 1.

Figure 4B:
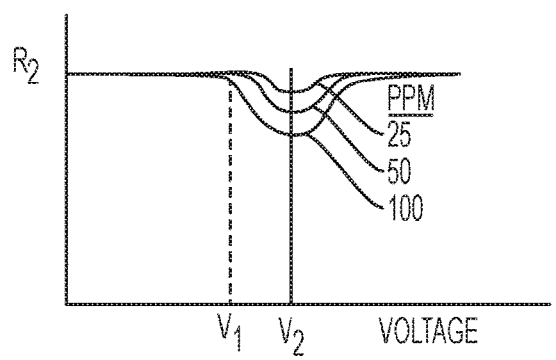
FIG. 4B is a graph of resistance versus voltage of a second contaminant at three different concentrations according to an exemplary embodiment of the present invention.

In FIG. 4B, a varying voltage may be applied to the above sensor in FIG. 4A while it is sensing a single contaminant but different from the contaminant in FIG. 4A. Sensing can occur at different contaminant concentrations and over an increasing voltage applied to the sensor. Resistance can be measured as the voltage increases. It can be seen from FIG. 4B that, for the particular contaminant in question, resistance $R_2$ drops from a baseline to a low or minimum (i.e., maximum resistance change) $R_{2MIN}$ at a voltage $V_2$. $R_{2MIN}$ may then be designated as a contaminant or sensor threshold 2. In embodiments, the threshold 2 can be a range. The threshold 2 can be determined at a plurality of contaminant concentrations to provide a different threshold for a respective different concentration of a single contaminant. For example, with three concentrations of contaminant 2, there may be thresholds 2A, 2B, 2C which do not overlap one another.

Accordingly, if a sensor is sensing an air flow, a varying voltage is being applied to the sensor, and sensor resistance drops to at least one of thresholds 2A-2C, at voltage $V_2$, one can conclude that contaminant 2 is present in the air flow. Knowing that contaminant 2 is present, one can then determine the source(s) of the contaminant from FIG. 3B. And, knowing which threshold 2A-2C was met or exceeded by the measured resistance, one can also determine the approximate concentration of contaminant 2.

Figure 4C:
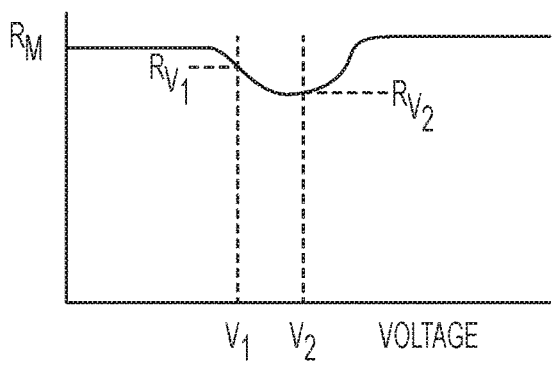
FIG. 4C is a graph of resistance versus voltage of mixed first and second contaminants according to an exemplary embodiment of the present invention.

FIG. 4C is a graph of resistance versus voltage according to an exemplary method of the present invention where two different contaminants are present in an air flow. In this example, the two contaminants are of unknown identity. A varying voltage may be applied to the above sensor in FIGS. 4A-4B while it is sensing the air flow. Sensing can occur while an increasing voltage is applied to the sensor. Resistance can be measured as the voltage increases.

It can be seen in FIG. 4C that a measured sensor response (i.e., resistance) $R_m$ exists at a baseline from zero voltage up to just before $V_1$. Just before $V_1$, $R_m$ begins to drop. At $V_1$, the resistance is $R_{V1}$. $R_m$ reaches a maximum low or change just before $V_2$. At $V_2$, resistance is $R_{V2}$. After $R_{V2}$, $R_m$ returns to the baseline.

If $R_{V1}$ at $V_1$ meets or exceeds one of thresholds 1A-1C established above, one may conclude that contaminant 1 exists in the air flow, at about a particular concentration, and comes from a particular source(s). If $R_{V2}$ at $V_2$ meets or exceeds one of thresholds 2A-2C established above, one may conclude that contaminant 2 exists in the air flow, at about a particular concentration, and comes from a particular source(s). Corrective action may then be taken vis-à-vis the above identified source(s).

Sensor Array Embodiment

In contrast to the "single sensor" embodiment above used to identify a plurality of contaminants, in this exemplary sensor array embodiment, an array of sensors is used to identify a plurality of contaminants so that any one sensor identifies only one respective contaminant. In this embodiment, a "sensor array" may be located in one or more of the positions occupied by the sensors 12 shown in FIGS. 1A-1B.

There can be any number of sensors in this embodiment. Each array can be optimized by sensor type and sensor output for each contaminant to be monitored. In other words, each sensor in the array can be tuned to a voltage that is optimal for a specific contaminant in order to obtain a maximum sensor response or contaminant signal for that contaminant. This array can permit using a range of sensor types, including metal oxide sensors each operating at a voltage tuned to a specific contaminant, electrochemical sensors, non-dispersive infra-red sensors, ultraviolet sensors, and other sensor types that would feed a contaminant output to the controller 11 and that would take an action based on the input from multiple sensors. In addition, an array of sensors can allow the user to isolate potential contamination to a source within the bleed air supply or from the cabin.

Wired Sensor Array

Figure 5:
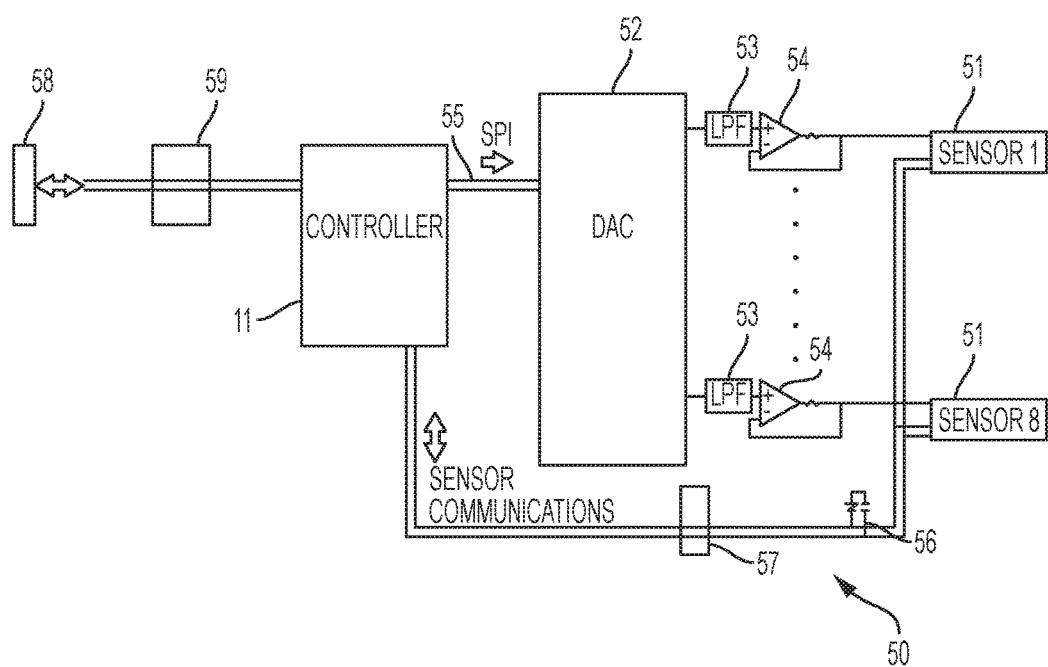
FIG. 5 is a wired circuit diagram for supplying voltage to a sensor array according to an embodiment of the present invention.

FIG. 5 is a schematic diagram of an exemplary wired sensor system or array 50 that can be employed in the ECS of FIGS. 1A-1B. The system or array 50 may include a plurality of sensors 51 that can take the place of one or more of the individual sensors 12 in FIGS. 1A-1B. The controller 11 can communicate with various components of the ECS as described above. From the sensors 51, sensor responses or contaminant signals (i.e., resistance signals) can be sent, via a wired circuit to the controller 11. The controller 11 may send signals to the sensor(s) to initiate operational checks, may send signals to initiate a reading if not operating in a continuous mode, or may tell the sensor(s) to increase sampling frequency when the controller determines that an increased frequency is required for system control.

In FIG. 5, the circuitry can provide multiple adjustable excitation voltages for an electronic gas sensor array and can provide data collection from the same gas sensor array for either ECS control or reporting to a higher level ECS controller. The microcontroller 11 can, via a host 59 (e.g., an ECS controller), provide an external host serial interface 58 (RS485, RS422, RS232, CANBUS etc) with signals for reporting of status or data to other processing units in the ECS system. A digital to analog converter (DAC) 52 can provide the conversion of a digital voltage value to an analog voltage. The DAC 52 is depicted as having, for example, eight channels of digital to analog conversion. The number of channels can be adjusted for each system requirement. During operation, firmware in the microcontroller 11 can use a non-proprietary serial interface (SPI, I2C etc) 55 to send digital update data to each channel of the DAC 52. When the DAC output is "enabled", the analog value of the each channel can conform to:

$$Vchannel = Vref * \frac{Channelvalue \text{ (bin)}}{Channelvaluemax \text{(bin)}}$$

The process of changing a digital value to analog value may not be "noiseless" and voltage transients can be expected from one or more of the outputs of the DAC 52. To minimize the application of voltage transients to the excitation input of the sensors 51, a low pass analog filter (LPF) 53 can be inserted to reduce the voltage transient while still giving adequate waveform fidelity for the sensor excitation.

Once the voltage transients from the DAC 52 are reduced with the LPF 53, an analog buffer amplifier 54 can be used to give a stable low impedance drive to the sensor excitation input.

Each sensor 51 can have processing electronics that will convert the process variable and provide electronics to allow for a multi-drop serial interface 57 to be used to collect the various sensor data.

During operation, firmware in the microcontroller 11 can use the non-proprietary serial interface (SPI, I2C etc.) 55 to "address" the channel of interest and "receive" the channel data. A serial bus 57 can use an "open collector" connection configuration which would require "pullup resistors" 56 to complete the interface connection.

Figure 6:
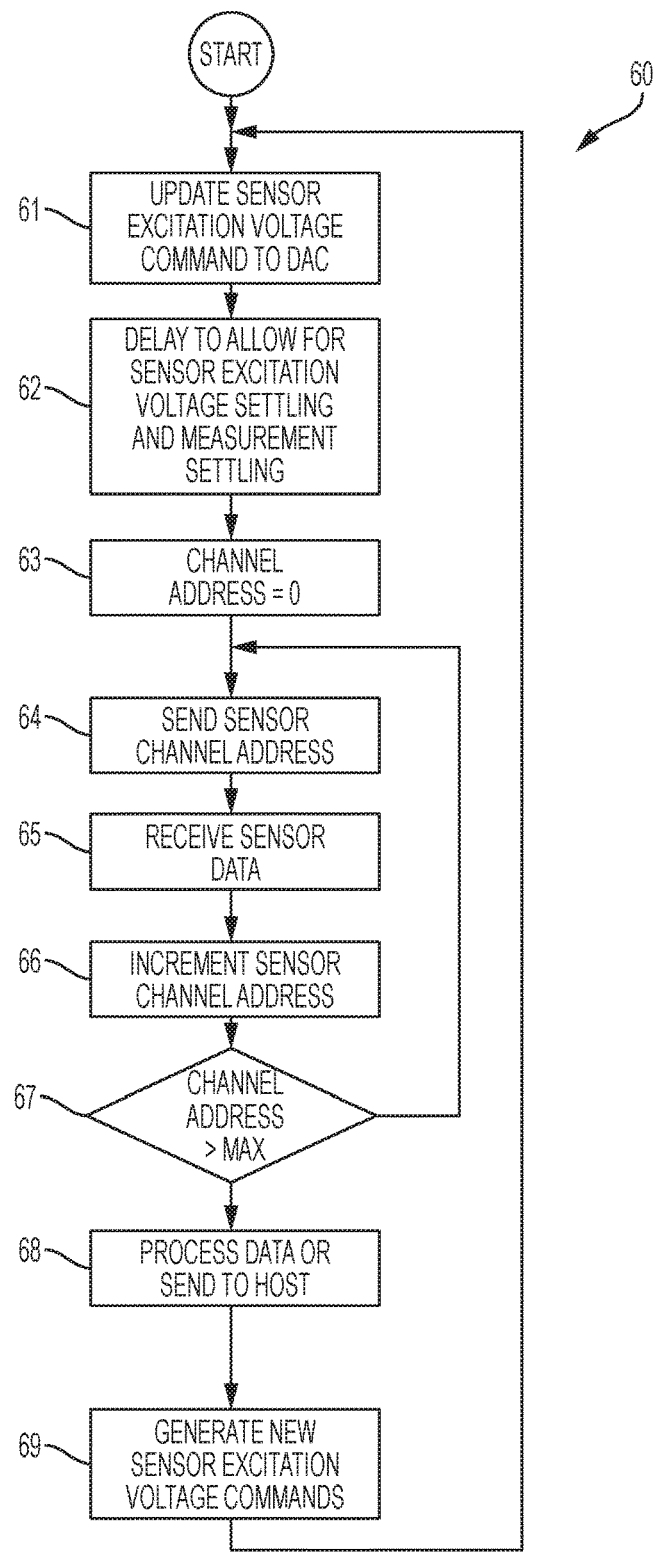
FIG. 6 is a flow chart of a method of supplying voltage to a sensor array according to the circuit of FIG. 5.

FIG. 6 is a flow chart of an exemplary method 60 of supplying voltage to a sensor array according to the circuit of FIG. 5. In a step 61, a voltage command may be sent to a digital-to-analog converter (DAC).

In a step 62, a periodic voltage sent to a sensor may be delayed between periods to allow for voltage settling and/or resistance measuring settling.

In a step 63, the controller 11 firmware may set the number of the first sensor to be measured/converted, and may be set to address the first of a plurality of sensors (e.g., "n" number of sensors).

In a step 64, the controller 11 may address the first of the plurality of sensors.

In a step 65, a controller 11 may receive data from the first of the plurality of sensors.

In a step 66, the controller 11 may be set to address the next of the plurality of sensors.

In a step 67, if the next sensor is not more than or equal to the nth sensor, then the method returns to step 64. If in step 67, the next sensor is greater than the nth sensor, the method proceeds to a step 68 wherein the controller may process data from the sensor and/or send data to a host.

In a step 69, the controller may generate new voltage commands.

Wireless Sensor Array

Figure 7:
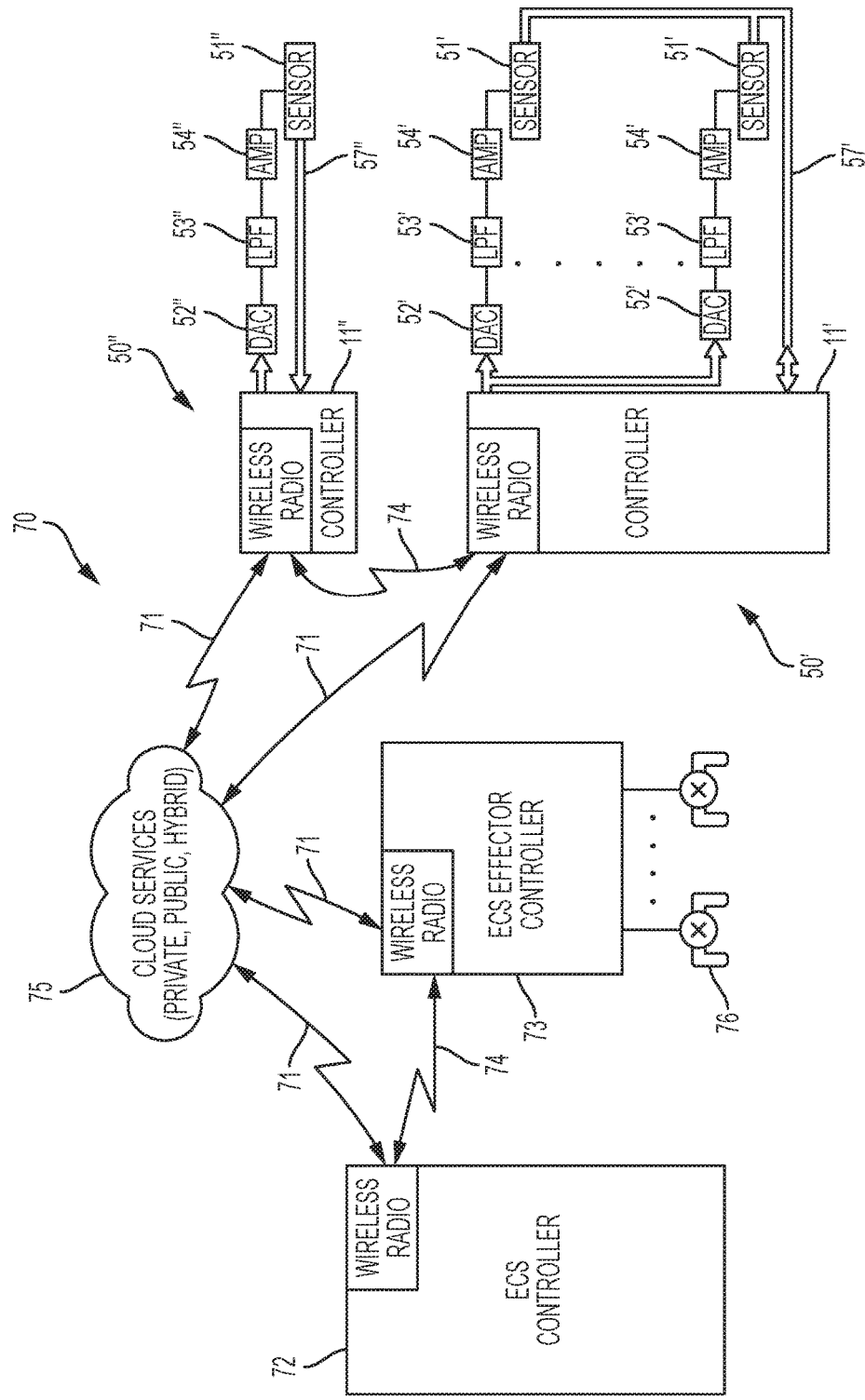
FIG. 7 is a wireless circuit diagram for supplying voltage to a sensor array according to an embodiment of the present invention.

FIG. 7 is a schematic diagram of an exemplary wireless sensor system or array 70. In the wireless system 70, the placement of system components/sensors is virtually unlimited with the proviso that the wireless signal can reach each of the components. Each component may require only a clear wireless path and electrical power. Complex control functions can be performed within each component and wireless communication will provide control and sensor data transfer.

In an exemplary embodiment, the system 70 may include a first sensor subsystem or subarray 50' and a second sensor subsystem or subarray 50" that can be employed in the ECS of FIGS. 1A-1B.

The first subsystem 50' may be configured in a fashion similar to the system 50 in FIG. 5. Accordingly, the first subsystem 50' may include a plurality of sensors 51' that can take the place of one or more of the individual sensors 12 in FIGS. 1A-1B. Each sensor can have a customized excitation voltage for increased sensor resolution of the contaminant being measured.

A controller 11' can communicate with various components of the ECS as described above. From the sensor(s) 51', sensor responses or contaminant signals (i.e., resistance signals) can be sent, via a wireless signal, to the controller 72. Alternatively, the sensor(s) 51' may contain an internal wireless circuit. Wireless components will potentially enable changes in the physical placement of ECS sensor and effector components without data cable changes. The controller 11' may send signals to the sensor(s) to initiate operational checks, may send signals to initiate a reading if not operating in a continuous mode, or may tell the sensor(s) to increase sampling frequency when the controller determines that an increased frequency is required for system control.

The first subsystem 50' may further include, with respect to each sensor 51', a respective digital to analog converter 52', a low pass analog filter 53', and an analog buffer amplifier 54', of which one or more of the foregoing can be similar in configuration and function as the digital to analog converter 52, the low pass analog filter 53, and the analog buffer amplifier 54 in FIG. 5.

The second subsystem 50" may include only a single sensor 51" that can take the place of one or more of the individual sensors 12 in FIGS. 1A-1B. Alternatively, the second subsystem 50" may include a plurality of sensors, such as that in the first subsystem 50'. A controller 11" can communicate with various components of the ECS as described above. From the sensor 51", sensor responses or contaminant signals (i.e., resistance signals) can be sent, via a wireless signal, to the controller 11". Alternatively, the sensor 51" may contain an internal wireless circuit. The controller 11' may send signals to the sensor to initiate operational checks, may send signals to initiate a reading if not operating in a continuous mode, or may tell the sensor to increase sampling frequency when the controller determines that an increased frequency is required for system control.

The second subsystem 50" may further include, with respect to the sensor 51", a respective digital to analog converter 52", a low pass analog filter 53", and an analog buffer amplifier 54", of which one or more of the foregoing can be similar in configuration and function as the digital to analog converter 52, the low pass analog filter 53, and the analog buffer amplifier 54 in FIG. 5.

A wireless connection(s) 71 (Wi-Fi, Bluetooth, proprietary, etc.) can be a connection to the "cloud services" 75. The "cloud services" 75 may tie all the system components together and can:

command changes in the individual sensor excitation waveforms, timing and absolute values;

receive data from each of the sensor channels;

store all ECS sensor data;

keep historical ECS sensor data;

transmit ECS sensor data to an ECS controller 72;

receive ECS Effector commands from the ECS controller 74;

transmit ECS Effector commands to an ECS Effector Controller 73; The ECS controller function can be put in the "cloud services" 75 to reduce wireless connections. From the ECS Effector Controller 73, commands may be sent to ECS components, such as a valve(s) 76.

A wireless connection(s) 74 (Wi-Fi, Bluetooth, proprietary, etc.) may allow for redundant sensor connections and wireless data paths if selected appropriately. For example, if the first subsystem 50' is in close proximity to the second subsystem 50" Bluetooth could be used to establish a data transfer channel between the first and second subsystems. If the first and second subsystems 50', 50" are tied to the "cloud services" 75 with Wi-Fi and if one of the subsystems 50, 50" loses Wi-Fi communications with the "cloud services", the other subsystem could get sensor data from the former, via Bluetooth 74, and transmit to "cloud services". There can be any number of subsystems in the system.

As shown in FIGS. 8A-8D, the varying voltage signals to the sensor(s) 51 can be in various non-linear forms, such as sinusoidal, square, and sawtooth. In any of the foregoing wave forms, it can be appreciated that a varying voltage is being provided in a continuous, multiple sweeping fashion over a range of voltages.

Figure 8A:
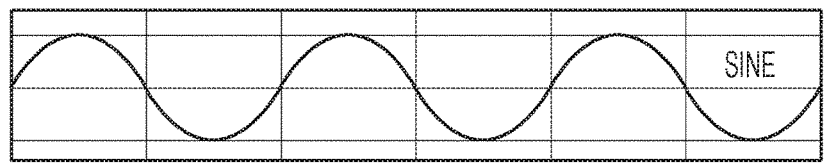
FIGS. 8A-8D are graphs of exemplary voltage waveforms generated according to embodiments of the present invention.
Figure 8B:
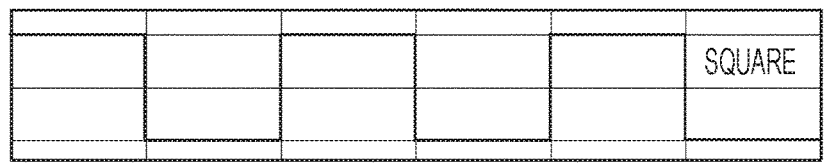
Figure 8C:
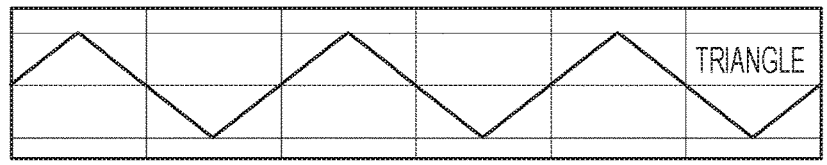
Figure 8D:
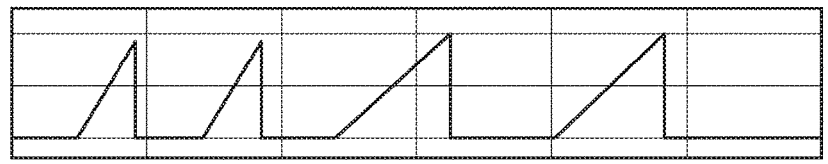

In FIG. 8D, according to an embodiment, the voltage signal can be a combination of sawtooth and square (i.e., modified sawtooth). The modified sawtooth waveform can allow for control parameters of peak excitation voltage, rate of change of excitation voltage, and the "off or sensor rest time". The peak voltage amplitude is to control the maximum excitation voltage applied to the sensor. The rate of change of applied excitation voltage gives the sensor the necessary "settling time" for repeatable sensor outputs. The "off or sensor rest time" is to allow the sensor to re-establish a new baseline before the start of the new scan.

The selection of the three control parameters can allow for sensor measurement cycles from fractions of seconds to tens of seconds. The DAC can allow for stable and repeatable voltage excitation of the sensor. The frequency of the waveform can determined by the time required for ramping plus the time required to provide the sensor with an adequate recovery or rest period in which the sensor reaches a stable baseline resistance. This baseline, though stable, may shift with time due to sensor contamination, thermal shift, aging of the resistivity of the semiconductor, or other unforeseen factors that may affect sensor performance.

FIG. 9 is an exemplary algorithm that describes potential corrective action that can be taken by the controller upon its receipt of a sensor signal.

It should be understood, of course, that the foregoing relates to exemplary embodiments of the invention and that modifications may be made without departing from the spirit and scope of the invention as set forth in the following claims.

We claim:

1. A contaminant detection system configured to provide a plurality of voltages from a voltage source to a sensor, wherein the voltage source provides the plurality of voltages to the sensor in a continuous, multiple sweeping fashion over a range of voltages that includes first and second voltages that are different from one another, the system comprising:

the sensor configured to respond to the first voltage and a second voltages;

wherein, in response to the first voltage, the sensor provides a first resistance response;

wherein, in response to the second voltage, the sensor provides a second resistance response that is different from the first resistance response;

a controller configured to receive signals from the sensor;

a look up table, which is accessible by the controller, and having data relating to contaminant name, contaminant concentration, contaminant source, sensor response, and applied voltage;

wherein, in response to determining that the first resistance response meets or exceeds a first threshold based on the sensor sending a first resistance signal to the controller, the controller determines a presence of a first contaminant and a source of the first contaminant;

wherein, in response to determining that the second resistance response meets or exceeds a second threshold based on the sensor sending a second resistance signal to the controller, the controller determines a presence of a second contaminant and a source of the second contaminant;

wherein, in response to determining the source of the first contaminant, the controller commands a first adjustment device outside of the contaminant detection system to adjust the source of the first contaminant; and wherein, in response to determining the source of the second contaminant, the controller commands a second adjustment device outside of the contaminant detection system to adjust the source of the second contaminant.

2. The system of claim 1, wherein the sensor is part of a sensor array.

3. The system of claim 1, wherein the plurality of voltages is in a non-linear wave form.

* * * * *